(12) United States Patent
Clay

(10) Patent No.: US 7,643,609 B2
(45) Date of Patent: Jan. 5, 2010

(54) SECONDARY X-RAY IMAGING TECHNIQUE FOR DIAGNOSING A HEALTH CONDITION

(75) Inventor: Haile Selassie Clay, Oakland, CA (US)

(73) Assignee: Andrea Clay, Oakland, CA (US)

( * ) Notice: Subject to any disclaimer, the term of this patent is extended or adjusted under 35 U.S.C. 154(b) by 44 days.

(21) Appl. No.: 11/619,192

(22) Filed: Jan. 3, 2007

(65) Prior Publication Data

US 2008/0159473 A1 Jul. 3, 2008

(51) Int. Cl.
G01N 23/223 (2006.01)
H05G 2/00 (2006.01)
(52) U.S. Cl. .............................. 378/45; 378/44; 378/119
(58) Field of Classification Search .................. 378/44, 378/45, 46, 119
See application file for complete search history.

(56) References Cited

U.S. PATENT DOCUMENTS

| | | | |
|---|---|---|---|
| 4,598,415 A | | 7/1986 | Luccio et al. |
| 5,247,562 A | * | 9/1993 | Steinbach .................... 378/119 |
| 5,495,515 A | | 2/1996 | Imasaki |
| 5,602,894 A | | 2/1997 | Bardash |
| 5,654,998 A | * | 8/1997 | Turcu et al. .................. 378/119 |
| 5,825,847 A | | 10/1998 | Ruth et al. |
| 6,035,015 A | * | 3/2000 | Ruth et al. ................... 378/119 |
| 6,226,354 B1 | * | 5/2001 | Mamine ....................... 378/119 |
| 6,332,017 B1 | | 12/2001 | Carroll et al. |
| 6,459,766 B1 | * | 10/2002 | Srinivasan-Rao ........... 378/119 |
| 6,724,782 B2 | * | 4/2004 | Hartemann et al. ............ 372/5 |

(Continued)

FOREIGN PATENT DOCUMENTS

JP 2000-088777 A 3/2000

(Continued)

OTHER PUBLICATIONS

Debrunner, Christian; Baker, Chris; Mahfouz, Mohamed; Hoff, William; Bowen, Jamon, "Tomographic reconstruction from an uncontrolled sensor trajectory", Colorado School of Mines, Golden, CO, United States, Conference: 2004 2nd IEEE International Symposium on Biomedical Imaging: Macro to Nano, Arlington, VA, United States, 20040415-20040418, (Sponsor: IEEE), 2004 2nd IEEE International Symposium on Biomedical Imaging: Macro to Nano 2004 2nd IEEE International Symposium on Biomedical Imaging: Macro to Nano v 2 2004. (IEEE cat n 04EX821), 2004.

(Continued)

*Primary Examiner*—Allen C. Ho
(74) *Attorney, Agent, or Firm*—SF Bay Area Patents LLC; Andrew V. Smith

(57) ABSTRACT

A beam of electronic charges and a standing wave laser beam are generated. The beam of charges is collided with the standing wave laser beam at a substantial angle to generate a burst cone of high energy x-rays. The x-ray cone is split, collimated and steered to a collapse point of diagnosis within a patient's body. A selected volume of the patient's body is scanned for diagnosis by directing subsequent burst cones at an array of points within the volume. The fluorescence spectra are detected from each of the points resulting from the high energy x-ray scanning. A chart is generated distinguishing fluorescence spectra emitted from various points within the volume.

6 Claims, 6 Drawing Sheets

U.S. PATENT DOCUMENTS

| | | | |
|---|---|---|---|
| 6,754,304 B1* | 6/2004 | Kumakhov | 378/45 |
| 7,016,470 B2* | 3/2006 | Lawrence et al. | 378/119 |
| 7,242,748 B2* | 7/2007 | Loewen et al. | 378/119 |
| 7,277,526 B2* | 10/2007 | Rifkin et al. | 378/119 |
| 7,295,653 B2* | 11/2007 | Loewen et al. | 378/119 |
| 7,310,408 B2* | 12/2007 | Filkins et al. | 378/119 |
| 7,382,861 B2* | 6/2008 | Madey et al. | 378/119 |
| 7,391,850 B2* | 6/2008 | Kaertner et al. | 378/118 |
| 2004/0044287 A1 | 3/2004 | Lin et al. | |
| 2005/0271185 A1 | 12/2005 | Loewen et al. | |
| 2006/0222147 A1 | 10/2006 | Filkins et al. | |
| 2006/0251217 A1 | 11/2006 | Kaertner et al. | |

FOREIGN PATENT DOCUMENTS

| | | |
|---|---|---|
| JP | 2001-155897 A | 6/2001 |
| WO | 2008/086062 A2 | 7/2008 |

OTHER PUBLICATIONS

Decraemer W F; Dirckx J J J; Funnell W R J., "Three-dimensional modelling of the middle-ear ossicular chain using a commercial high-resolution X-ray CT scanner", Biomedical Physics, University of Antwerp, RUCA, Antwerpen, Belgium. wim.decraemer@ua.ac.be Journal of the Association for Research in Otolaryngology—JARO (United States), Jun. 2003 , 4, (2), p. 250-63, Publishing Model Print.

Endo, Masahiro; Kamagata, Nozomu; Sato, Kazumasa; Hattori, Yuichi; Kobayashi, Shigeo; Mizuno, Shinichi; Jimbo, Masao; Kusakabe, Masahiro, "Development of a 3D CT scanner using cone beam", Natl. Inst. of Radiological Sciences, Chiba-shi, Jpn, Conference: Medical Imaging 1995: Physics of Medical Imaging, San Diego, CA, USA, 19950226-19950227, (Sponsor: SPIE—Int Soc for Opt Engineering, Bellingham, WA USA), Proceedings of SPIE—The International Society for Optical Engineering v 2432 1995. Society of Photo-Optical Instrumentation Engineers, Bellingham, WA, USA. p. 291-297, 1995.

Endo M; Yoshida K; Kamagata N; Satoh K; Okazaki T; Hattori Y; Kobayashi S; Jimbo M; Kusakabe M; Tateno Y., "Development of a 3D CT-scanner using a cone beam and video-fluoroscopic system," Research Center of Charged Particle Therapy, National Institute of Radiological Sciences, Chiba, Japan., Radiation medicine (Japan) , Jan.-Feb. 1998, 16, (1), p. 7-12, Publishing Model Print.

La Riviere Patrick J, "Approximate analytic reconstruction in x-ray fluorescence computed tomography", Department of Radiology, The University of Chicago, Chicago, IL 60637, USA. pjlarivi@midway. uchicago.edu Physics in medicine and biology (England), Jun. 7, 2004, 49, (11), p. 2391-405, Publishing Model Print.

Hoff, William, et al "Three-Dimensional Determination of Femoral-Tibial Contact Positions Under in vivo Conditions Using Fluoroscopy", http:citeseer.ist.psu.edu/471039.html, Presented at the European Society of Biomechanics, Leuven, Aug. 28-31, 1996, and received the Clinical Biomechanics Award, 19 pages.

Shanjen Pan; Wenshan Liou; Ang Shih; Mun-Soo Park; Ge Wang; Newberry, S.P.; Hyogun Kim; Shinozaki, D.M.; Ping-Chin Cheng, "Experimental system for X-ray cone-beam microtomography," Dept. of Electr. & Comput. Eng., State Univ. of New York, Buffalo, NY, USA, Microscopy and Microanalysis, vol. 4, No. 1 , p. 56-62, Publisher: Springer-Verlag, 1998.

Shih, Ang, Abstract for "Table-mapping cone-beam X-ray tomography algorithm and two-photon data storage system", Ph.D., 2000, State University of New York at Buffalo, Adviser: Ping-Chin Cheng, vol. 61/09-B of Dissertation Abstracts International. p. 4899, Order No. AADAA-I9987101 (191 Pages).

Vincze Laszlo; Vekemans Bart; Brenker Frank E; Falkenberg Gerald; Rickers Karen, Somogyi Andrea; Kersten Michael; Adams Freddy, "Three-dimensional trace element analysis by confocal X-ray microfluorescence imaging", MiTAC, University of Antwerp, Universiteitsplein 1, B-2610 Wilrijk, Belgium. laszlo.vincze@ua.ac. be, Analytical chemistry (United States) , Nov. 15, 2004 , 76, (22), p. 6786-91, Publishing Model Print.

Wiegert, J.; Bertram, M.; Schafer, D.; Conrads, N.; Timmerc, J.; Aach, T.; Rose, G., "Performance of standard fluoroscopy anti-scatter grids in flat detector based cone beam CT", Institute for Signal Processing University of Lubeck, 23538 Lubeck, Germany, Conference: Medical Imaging 2004: Physics of Medical Imaging , San Diego, CA, United States , 20040215-20040217, (Sponsor: SPIE), Proceedings of SPIE—The International Society for Optical Engineering Medical Imaging 2004: Physics of Medical Imaging v 5368 n 1 2004., 2004.

Agafonov, Alexey V., et al., "Spectral charateristics of an advanced x-ray generator at the KIPT based on Compton backscattering", Fourth-Generation X-Ray Sources and Ultrafast X-Ray Detectors. Edited by Tatchyn, Roman O.; Chang, Zenghu; Kieffer, Jean-Claude; Hastings, Jerome B. Proceedings of the SPIE, vol. 5194, pp. 20-29 (2004).

Roman Tatchyn, "Pulsed Laser Undulators Excited by Compact Storage Rings: A Candidate Technology for Single-shot Medical Imaging", presented on Aug. 8, 2003, 28 pages, IAC Medical Imaging Workshop, Pocatello, Idaho; Medical and Biological Imaging with Novel X-ray Beams, Aug. 7 and 8, 2003.

Matthew Nguyen, "A Simulation of a Proposed Technique for Medical Imaging," SSRL (Stanford Synchrotron Radiation Laboratory), Advisor: Dr. Roman Tatchyn, Summer 1999, 26 pages.

Internet printout from NSC International Cooperation Sci-Tech Newsbrief, Profile of the European Synchrotron Radiation Facility (ESRF), Author : Science Division/Taipei Economic and Cultural Representative Office in France Position : Science Division/Taipei Economic and Cultural Representative Office in France, Article Source : Science Division/Taipei Economic and Cultural Representative Office in France http://stn.nsc.gov.tw/en/view_detail. asp?doc_uid=0920909001, published Sep. 9, 2003, 7 pages.

Richard Fitzgerald, "Phase-Sensitive X-Ray Imaging, New approaches that can detect x-ray phase shifts within soft tissues show promise for clinical and biological applications" Physics Today, 53 (7), 23-27 (2000).

Paul L. Csonka, "Secondary X-ray Imaging: an alternative approach to angiography and other applications" Nuclear Instruments and Methods in Physics Research Section A: Accelerators, Spectrometers, Detectors and Associated Equipment, vol. 431, Issues 1-2, Jul. 11, 1999, pp. 306-319.

Internet printout from John Muir Mt. Diablo, "Stereotactic Radiosurgery (SRS)—Shaped Beam Surgery: New technology offers non-invasive treatment options", http://www.jmmdhs.com/index.php/stereotactic.html, printed Jul. 22, 2004, 4 pages.

Internet printout, "Cancer—What is it? A cancer is an uncontrolled proliferation of cells", http://users.rcn.com/jkimball.ma.ultranet/BiologyPages/C/Cancer.html, printed Dec. 22, 2005, 5 pages.

Recent Advances in Medical Applications of Synchrotron Radiation, Workshop Agenda and Abstracts, Stanford Synchrotron Radiation Laboratory/SLAC, Menlo Park, California, Mar. 4-5, 2002, pp. i and 1-22.

Internet printout from ELECTTRA, "BL 6.1 R SYnchrotron Radiation for MEDical Physics (SYRMEP)", http://www.electtra.trieste. it/experiments/beamlines/syrmep/, printed May 20, 2004, 3 pages.

Internet printout from Center for Radiation Therapy and Biomedical Research—a satellite institute of Candle, "Clinical Application of SR on Candle", http://www.candle.am/medical.htm, printed May 20, 2004, 4 pages.

"Risks of Radiation", Journal of Longevity, 2005, vol. 11, No. 9, p. 26.

"First Specific Evidence Cancer Can Be Killed", Journal of Longevity, 2004, vol. 10, No. 12, p. 36.

Cele Abad-Zapatero, Abbott Laboratories, Keynote Speaker, "The Impact of Synchrotron Radiation in Biotechnology: Present and Future", Opportunities for Synchrotron Light in Biotechnology, Biopharmaceuticals and Medicine, Summary of Presentations at the Workshop, Toronto, Dec. 3, 4 1997, organized by L. Delbaere (chair) and E. Pai, sponsored by CISR, CLS, NRC, PMAC, 4 pages.

Internet printout from The ICF Quarterly Report, Jan.-Mar. 1996, "$2^{nd}$ Quarter 1996 Summary (in its entirety)", http://www.llnl.gov/nif/icf/icfpubs/qrtly_reports/jan_mar96/jan96.html, printed Feb. 6, 2004, 3 pages.

Internet printout from Background on the Nobel Prize in Physics 1997 for Professor Steven Chu, Stanford University, Stanford, CA, USA, Professor Claude Cohen-Tannoudji, Collège de France and École Normale Supérieure, Paris, France, and Dr. William D. Phillips, National Institute of Standards and Technology, Gaithersburg, MD, USA,, for "development of methods to cool and trap atoms with laser light" http://physics.nist.gov/News/Nobel/OtherSites/phyback97.html, 7 pages.

Internet printout from User Case for Candle, "Making User Case for Candle", http://www.candle.am/usercase.html, printed Oct. 25, 2004, 10 pages.

W. Thomlinson, "Medical applications of synchrotron radiation", Nuclear Instruments and Methods in Physics Research Section A, Aug. 1992, vol. 319, Issue 1-3, p. 295-304.

Internet printout from Imaginis, Medical Procedures, "Computed Tomography Imaging (CT Scan, CAT Scan)", printed Feb. 26, 2006, http://imaginis.com/ct-scan/how_ct.asp, 2 pages.

Internet printout from Mayo Clinic, "New CT Scanner Breaking New Ground in Medical Imaging", printed Feb. 26, 2006, http://www.mayoclinic.org/radiology-rst/somatom.html, 2 pages.

Internet printout from Molecular Imaging Services, Inc., "64 slice CT scanner can quickly and accurately image coronary arteries non-invasively", printed Feb. 26, 2006, http://www.mismedical.com/ct.php, 2 pages.

Internet printout from PENN Medicine, Press Release Sep. 29, 2005, "New Use of 64-Slice CT Scan to be Studied at HUP to Help Diagnose Coronary Artery Disease in the Emergency Department", printed Feb. 26, 2006, http://www.uphs.upenn.edu/news/News_Releases/sep05/64sliceCT.htm, 2 pages.

Julie Sevrens Lyons, "Scanner reveals hidden threats", Internet printout from www.mercurynews.com, posted Feb. 14, 2006, printed Feb. 26, 2006, 3 pages.

G. Michael Bancroft, "Synchrotron Radiation: The Most Versatile Spectroscopic Source", Internet printout from http://www.innovation.ca/innovation2/essay_bancroft.html, printed May 20, 2004, 3 pages.

Andreas K. Freund, et al., "Time Structure of X-Ray Sources and Its Applications", Abstract Internet printout from Proceedings vol. 3451, ISBN: 0-8194-2906-6, 216 pages, Published 1998, Meeting Date: Jul. 19-24, 1998, San Diego, California, http://www.spie.org/web/abstracts/3400/3451.html, printed Mar. 1, 2004, 15 pages.

Internet printout from Scienceworld.wolfram.com, "Standing Wave", http://scienceworld.wolfram.com/physics/StandingWave.html, printed Feb. 7, 2004, 4 pages.

Internet Paper: High energy rays, From Wikipedia, the free encyclopedia, Retrieved from "http://en.wikipedia.org/wiki/High_energy_rays" on May 30, 2008, 3 pages.

Klaus-Dieter Liss, Arno Bartels, Andreas Schreyer, Helmut Clemens, High-Energy X-Rays: A Tool For Advanced Bulk Investigations in Materials Science and Physics, Textures and Microstructures, Taylor & Francis Ltd., vol. 35, No. 3/4, Sep./Dec. 2003, pp. 219-252.

Klaus-Dieter Liss, Arno Bartels, Helmut Clemens, Slawomir Bystrzanowski, Andreas Stark, Thomas Buslaps, Frank-Peter Schimansky, Rainer Gerling, Christina Scheu, Andreas Schreyer, Recrystallization and phase transitions in a c-TiAl-based alloy as observed by ex situ and in situ high-energy X-ray diffraction, Acta Materialia 54 (2006) 3721-3735.

Internet Paper: Radiographic equipment, From Wikipedia, the free encyclopedia, Retrieved from "http://en.wikipedia.org/wiki/Radiographic_equipment" on Mar. 28, 2008, Categories: Medical imaging—Radiation—Nuclear technology—Radioactivity—Radiography 4 pages.

Internet Paper: "SAIC: Products: Relocatable VACIS Inspection System: Frequently Asked Questions" Retrieved from "http://www.saic.com/products/security/relocatable-vacis/relocatable-vacis-faq.html" on Sep. 29, 2007, 7 pages.

PCT Notification of Transmittal of the International Search report and the Written Opinion of the International Searching Authority, or the Declaration, for PCT Application No. PCT/US2008/050052, paper dated May 28, 2009, 8 pages.

Opportunities for Synchrotron Light in Biotechnology, Biopharmaceuticals and Medicine, Summary of Presentations at the Workshop, Toronto, Dec. 3, 4 1997, organized by L. Delbaere (chair) and E. Pai, sponsored by CISR, CLS, NRC, PMAC, 4 pages.

* cited by examiner

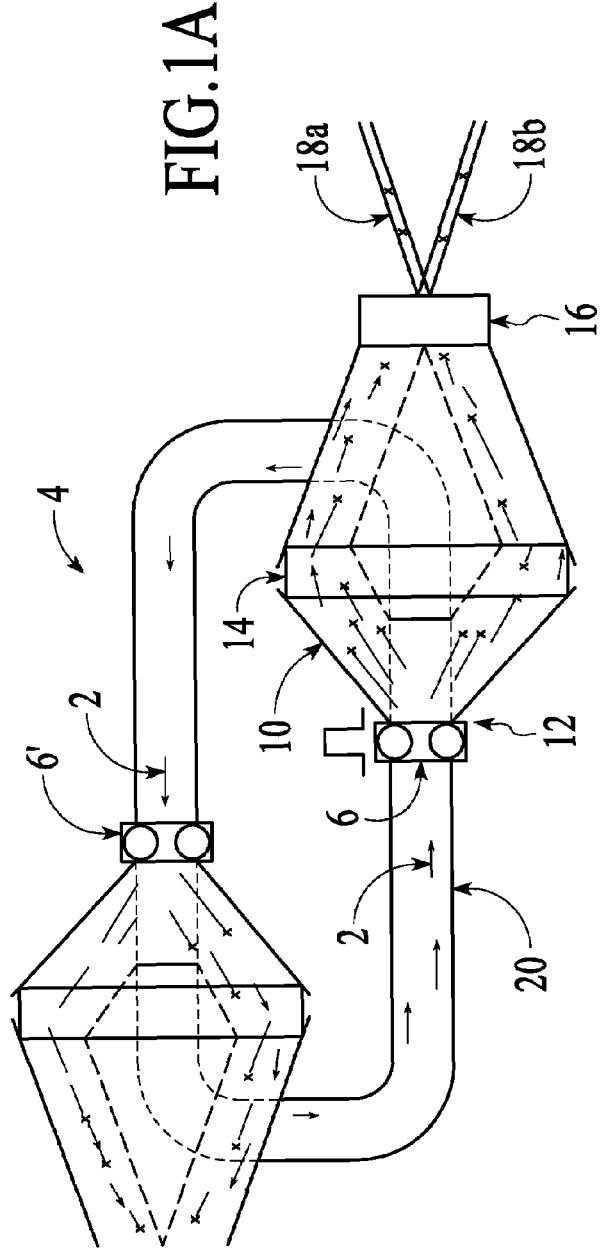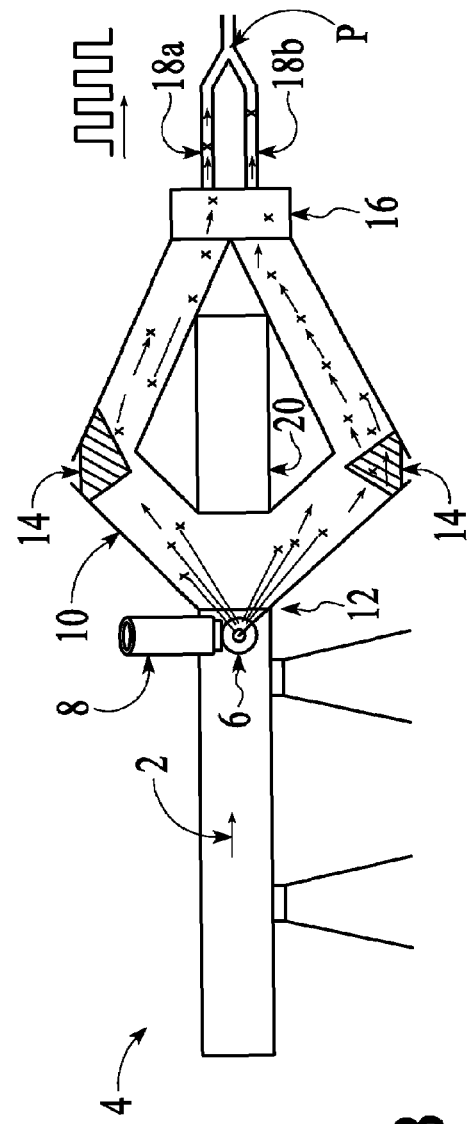

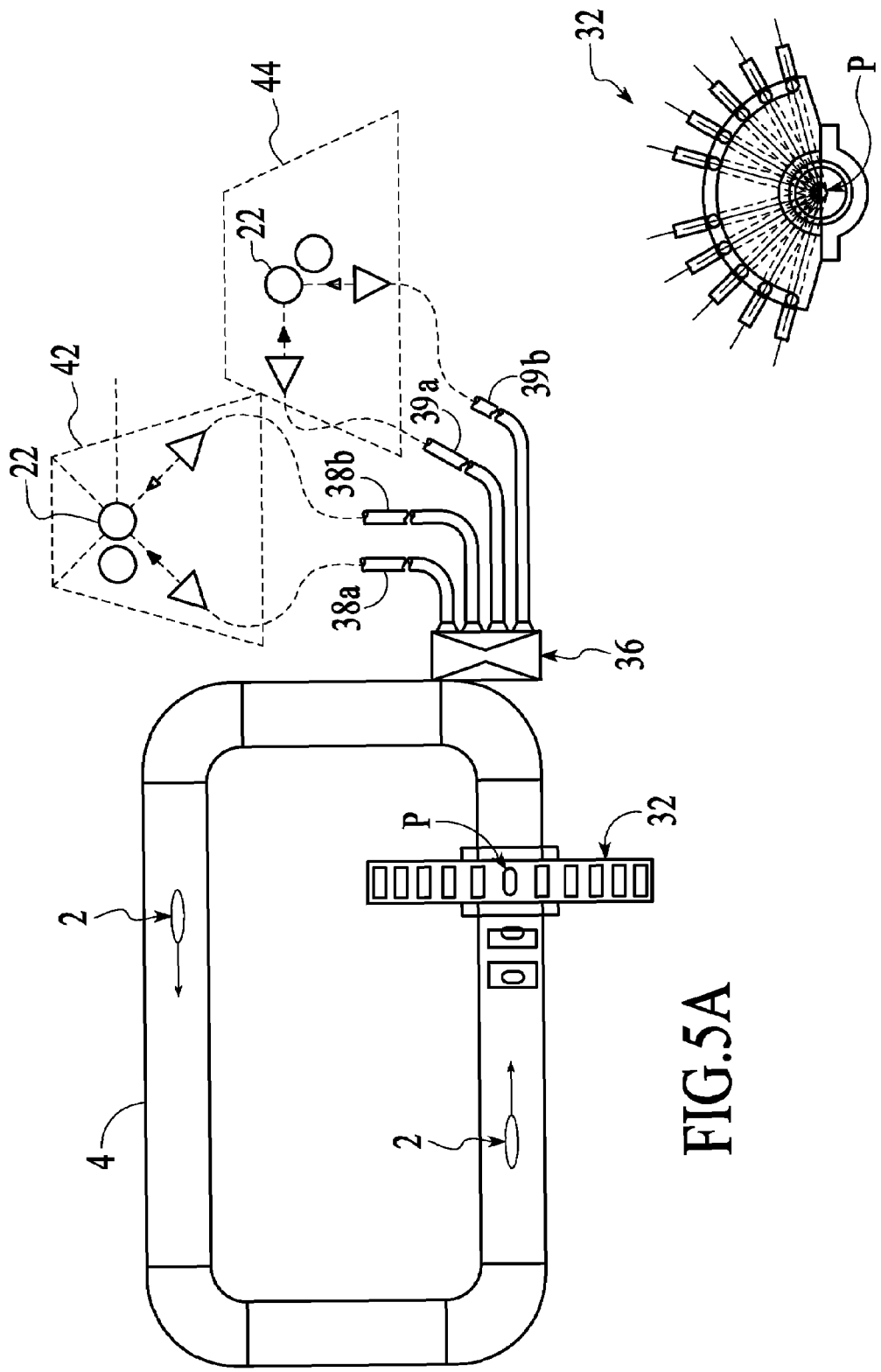

SECONDARY X-RAY IMAGING TECHNIQUE FOR DIAGNOSING A HEALTH CONDITION

REFERENCE TO DISCLOSURE DOCUMENT

Reference is here made to disclosure document no. 559224.

BACKGROUND

1. Field of the Invention

The invention relates to medical diagnosis, and particularly to secondary x-ray imaging for diagnosing a medical condition.

2. Description of the Related Art

Synchrotron X-Radiation

W. Tomlinson has provided a comprehensive survey article entitled, "Medical Applications of Synchrotron Radiation", at Nuclear Instruments and Methods in Physics Research A319 (1992) 295-30, which is incorporated by reference. There, Tomlinson accounts regarding clinical medicine and basic research using synchrotron x-rays. Radiography, angiography, CAT and PETT scanning, mammography and nuclear medicine are examples of technologies developed to image the human anatomy.

CAT Scan

X-ray imaging techniques such as radiography and CT scanning have been immensely valuable in medicine and, to a lesser extent, in industry. In such techniques, the X-ray absorption along X-ray paths generates a shadow-gram of the object's structure. It is desired to use secondary x-ray imaging using detected fluorescent X-radiation, together with knowledge of the parameters of the incident beam, to reconstruct 3D and 4D properties of precise object volumes in a much more informative way. Such will provide enhanced signal-to-noise ratio, sharpened imaging of the structure of the object, and specific knowledge of the chemical composition.

Medical Diagnostics: Cancer and Angiography

Effective treatments for cancer and heart ailments are among those that have been and are being the most actively sought in medical science. External and internal sources of radiation have been used in the battle against cancer. Although useful, internal ingestion of radioactive iodine can be hazardous to the patient. It is desired to have an external diagnostic technique that can provide a precision three-dimensional map of a cancerous area and/or a three or four dimensional understanding of a cardiac patient's beating heart.

Most current diagnostic methods produce two-dimensional images. These can provide information, but not a precision knowledge of the volumetric space being occupied by a cancerous area or other internal problem of a patient. A three-dimension technique that would rotate a patient who is juxtaposed along an x-radiation beam path would be difficult for a patient to endure and would involve too much relative patient motion with respect to the beam along with changing body contours that scatter and absorb radiation differently. Such system also has its own mechanical complexities. It is desired to have a technique for producing three-dimensional images using secondary x-rays without rotating the patient. Moreover, it is desired to have technique that provides four-dimensional images, i.e., showing a temporal component particularly for cardiac monitoring.

Producing X-Rays by Electron-Photon Collisions

Conventional x-ray techniques can provide two-dimensional images of bones and other internal structures of a human body. These can provide insight mostly into shapes and densities of those internal structures, but not to specific compositions of tissues. Biopsies are often performed in order to understand specific compositions of tissues under study. However, invasive techniques such as biopsies are less desirable to patients for many reasons including enhanced effort and cost compared with a non-invasive technique. It is desired to have a non-invasive technique which provides specific information relating to compositions of tissues under study.

Roman Tatchyn of the Stanford Synchrotron Radiation Laboratory has studied electron-photon collisions for generating x-rays including pulsed laser undulators excited by compact storage rings. In ICA Medical Imaging Workshop at Pocatello, Id., incorporated by reference, Mr. Tatchyn describes a technique for interacting an electron beam with in parallel with a laser or microwave cavity. Alignment and component requirements on the system render a practical tool difficult to achieve and operate.

U.S. Pat. No. 5,825,847 to Ronald Ruth, et al., incorporated by reference, discloses a further technique for interacting a laser beam with an electron beam for generating secondary x-rays from electron-photon collisions. An intense pulse from a high power laser, stored in a high finesse resonator is repetitively collided nearly head-on with an electron bunch. The photons are intended to Compton backscatter from the electron bunch. The timing of the photon pulse and the electron bunch to contemporaneously arrive at the interaction region 26, of FIG. 1 of Ruth et al., has to be very precise. FIG. 4 of Ruth et al. illustrate the electron bunch and laser pulse bearing down on the interaction region at the same time. It is desired to have a technique that does not require such precision timing.

Standing Wave Laser Beams

It is possible to provide a laser arrangement for generating a standing wave beam. Such beam oscillates, but does not propagate. U.S. Pat. Nos. 6,111,906, 6,144,743, 5,933,440, 5,834,769, and 4,992,656, all incorporated by reference, for example, describe various standing wave laser beam environments. The inventor in this present application has recognized that interacting electron pulses with a standing wave laser beam, as opposed to a traveling photon packet or laser pulse, provides an arrangement with relaxed temporal and alignment precision requirements.

BRIEF SUMMARY OF THE INVENTION

A method of scanning a patient with radiation is provided for diagnosing a condition. A beam of electronic charges and a standing wave beam are generated. The beam of charges is collided with the standing wave laser beam, including intersecting the standing wave laser beam and beam of charges at a substantial angle to generate a burst cone of high energy x-rays. The x-rays are split, collimated and steered, preferably magnetically, to a collapse point of diagnosis within a patient's body. A selected volume (3-D) of the patient's body is scanned for the diagnosis by directing subsequent burst cones at an array of points within the volume. Fluorescence spectra are detected from each of the points resulting from the high energy x-ray scanning.

The method may further include analyzing the fluorescence spectra to determine tissue properties. The scanning and detecting of the selected patient volume may be repeated to obtain temporal information (4-D). The selected volume may be scanned without rotating the patient relative to the propagation direction of the burst cones. The burst cone may be collimated and split into multiple pathways for sequential incidence at points within the volume. The standing wave laser beam may be generated by intersecting two beams powered with a same power supply for relatively temporally controlling said two beams, and a single beam may be split, wherein the split beams are then intersected for providing relative temporal control of the split beams.

A chart may be generated of the selected volume of the patient's body distinguishing fluorescence spectra from various points within the volume.

A system is also provided for scanning the patient with radiation to diagnose a condition. A set of one or two or even several lasers generate the standing wave laser beam disposed in the path of an electron synchrotron beam including high speed electron bunches. Pulses of secondary x-rays are generated by pulsed interactions between the electron bunches and the standing wave beams. An x-ray collimator captures one or more burst cones of secondary x-rays generated from collisions between the electron beam and the standing wave laser beam. A steering arrangement directs the secondary x-ray burst cones for scanning an array of points within a selected volume of a patient's body. A fluorescence detector captures fluorescence spectra emanating from the array of points within the patient volume.

A computer may be used for analyzing the fluorescence spectra to determine tissue properties. The x-ray collimator may include a splitter for generating two pathways of burst cones. The set of lasers may generate the standing wave laser beam including two lasers powered with a same power supply for relatively temporally controlling the two beams. The set of lasers may generate the standing wave laser beam including a single laser and optics for splitting a single beam and intersecting the split beams for providing relative temporally control of the split beams.

BRIEF DESCRIPTION OF THE DRAWINGS

FIG. 1A is an overhead view which schematically illustrates a system for generating secondary x-rays in accordance with a preferred embodiment.

FIG. 1B is a side view of the system of FIG. 1A.

FIG. 5A is an overhead view which schematically illustrates a system for generating secondary x-rays in accordance with another embodiment.

FIG. 5B is a side cross-section view of a particle beam-standing wave laser beam interaction portion of the system of FIG. 5A.

DETAILED DESCRIPTION OF THE EMBODIMENTS

Figure 2A:
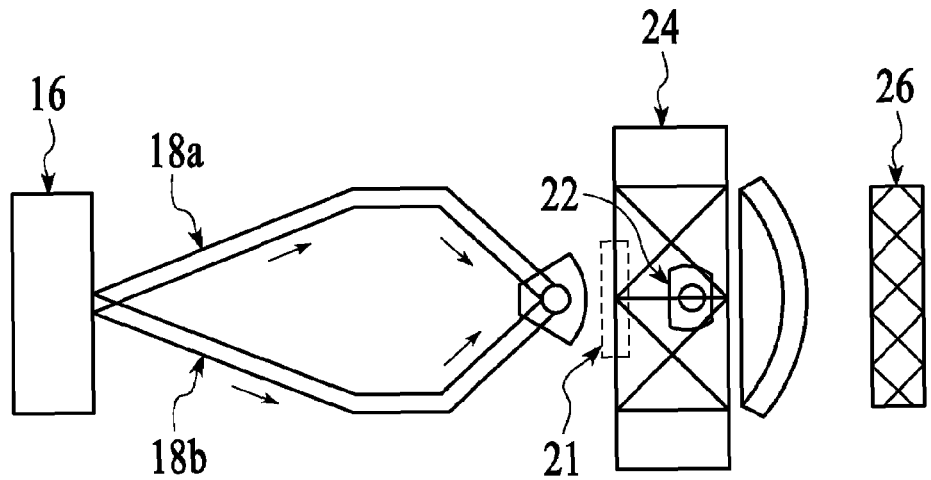
FIG. 2A is an overhead view which schematically illustrates a magnetic steering section for combining with the system of FIG. 1A for generating a secondary x-ray beam for medical diagnosis.

Embodiments are provided below including three and four dimensional high energy x-ray systems (3D and 4D HEX-R Systems).

3D Secondary X-Ray Imaging (3DSXI)

Referring to FIGS. 1A and 1B, which show overhead and side views, respectively, a set of bunched, high energy electrons 2 are generated by a synchrotron radiation (SR) machine 4. Those electrons 2 may be caused to flow directly into a confined space that is occupied by a standing wave 6 of photons generated by a standing wave laser 8. The set of electrons 2 may be flowed through the standing wave 6, and optionally a second standing wave 6', without commingling of the beams 2 and 6. High energy x-rays (HEX) 10 are expelled in the direction of the flow of the electrons 2 in the shape of a truncated cone array of HEX(s) 10 that appears to start at the outer most diameter 12 of the electron beam 2. Multiple pathways of burst cones are split having identified power and configuration, and each is directed to a specified point of an array of points that are scanned sequentially within a volume of a subject, e.g., a human heart, brain or other organ or portion of an organ.

Figure 4B:
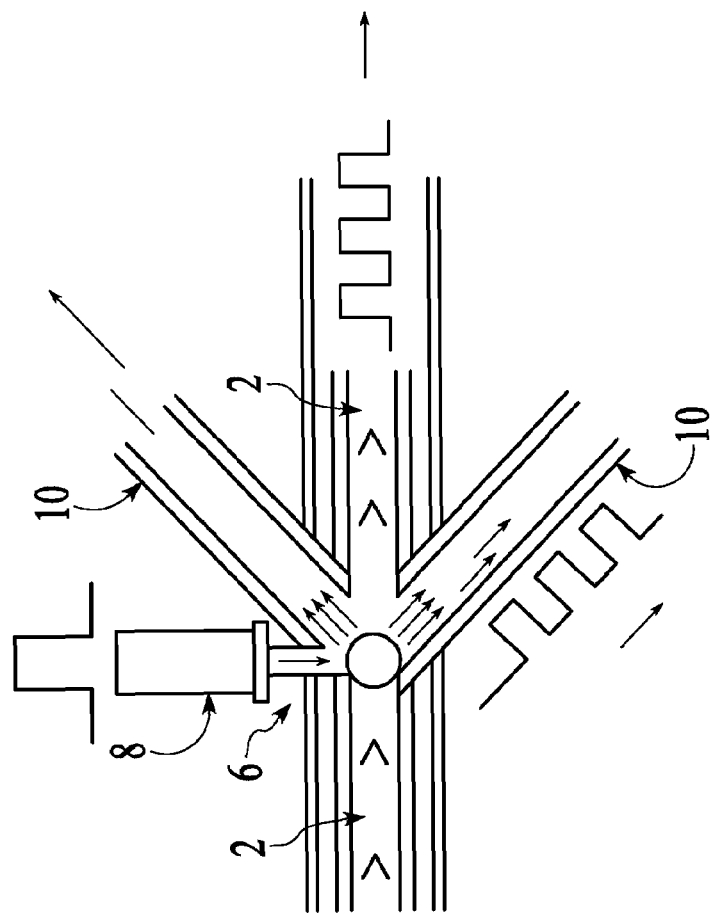
FIG. 4B is an side view which schematically illustrates a transverse interaction between a standing wave laser beam and an electron beam.
Figure 4A:
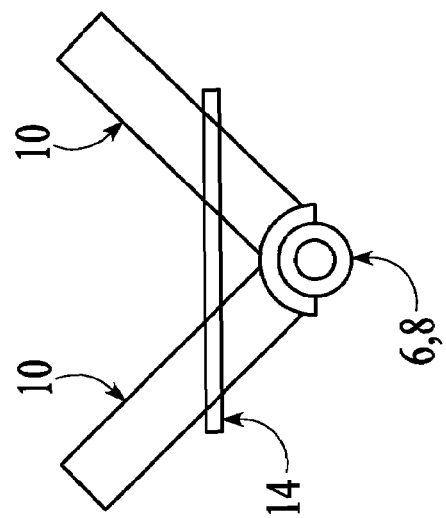
FIG. 4A is an overhead view which schematically illustrates a transverse interaction between a standing wave laser beam and an electron beam.

FIGS. 4A and 4B illustrate interaction of the high energy electrons 2 with a standing wave laser beam. The secondary x-rays are generated and propagate away from the interaction site as high energy x-rays (HEX) 10. The overhead view of FIG. 4A and the side view of FIG. 4B each show two symmetric secondary x-ray beam paths propagating away from the interaction site with the high energy electrons, because each represents a cross-sectional view. The secondary x-rays propagate in a three-dimensional continuous cone of radiation.

Standing Wave Laser Beam

In U.S. Pat. No. 5,825,847, a pulsed laser beam is generated and provided at an interaction zone, wherein photons interact with electrons whirling at high speed within a synchrotron to produce high energy x-rays. In a preferred embodiment of the present invention, high speed electrons interact with an array of standing waves of photons. The array of standing waves is generated by a set of one or more, and preferably several, standing wave lasers. The location of the standing waves is fixed in a defined space, so as to be easily disposed in the direct path of bunches of high energy electrons that flow within a Storage Ring of a synchrotron particle accelerator. The interaction of the high-energy electron beam and the standing wave of photons of the laser(s) provides advantageous results.

The electron bunch continues along its path without hindrance or co-mingling with the standing wave. However, the electrons do lose increments of relativistic mass and/or energy, which results in a cooling effect, or a tighter bunching. As a result, quanta of high energy x-rays, or HEX-rays, are produced in the shape of a truncated cone, which starts at the outermost circumferences of the bunched electrons and extends outward, in the direction of the flow of the electrons.

Magnetic Steering

The cone array of HEX(s) 10 is then collected using a magnet 14 or other beam steering device as understood by those skilled in the art. The beam is approximately equally split and guided by a magnetic, electrical, optical, magneto-optical, electro-optical, magneto-electrical or magneto-electro-optical collimating subcomponent 16 into two, or more, collimated beams 18a and 18b that are preferably, but not necessarily, identical in magnitude. As illustrated in the overhead view of FIG. 1A, the magnet 14 may extend above and/or below a vacuumed chamber 20 that houses the synchrotron machine. The collimators 16 generate two identical traveling waves 18a, 18b of HEX-R beams that are preferably physically identical in multiple respects. The HEX-rays are preferably magnetically deflected into two identical collimators that begin at the circumference of the electron beam channel and extend above and below the housing of the synchrotron machine.

The HEX beams are then independently channeled to a contiguous set of collimating and bending magnets so as to cause the beams to intersect in the same plane at a 90 degree angle. This intersection point is magnetically scanned in the X-Y-Z planes so as to create a 3D view of a specified volume, e.g., an internal organ or a cancerous or otherwise physiologically suspect region of a human being. The SXI data is captured by detectors and transmitted to a computer for reconstructing 3D and 4D photo images as well as their chemical compositions. The different chemical compositions are possible to discern, because unique fluorescences are achieved when different compositions of tissues are scanned. A guide laser beam may be provided, e.g., attached to element 24 of FIG. 2A, or to element 21 that supports the raster, for aligning the subject. Sequentially the raster 21 sweeps the subject 22 for an adjustable period of about 5-50 or 100 nanoseconds, or approximately 20 nanoseconds.

Figure 3A:
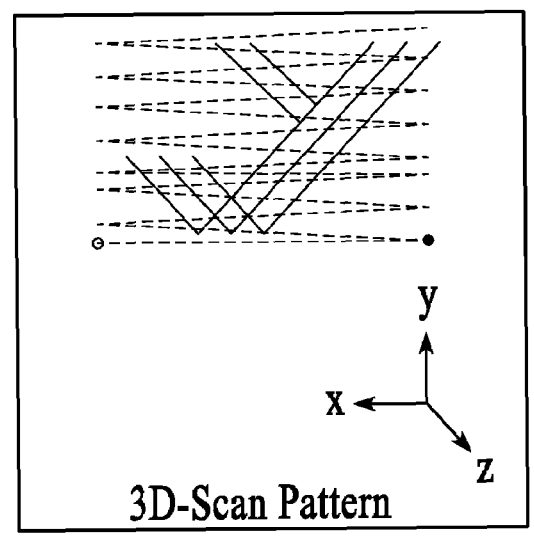
FIG. 3A schematically illustrates a scan pattern for the system of FIGS. 1A-2B.

In the embodiment of FIG. 1B, the two traveling wave beams 18a, 18b of HEX-R(s) travel in the same plane as the contiguous vacuum chamber 20. FIG. 1A shows the beams 18a and 18b being magnetically guided to cross at a fixed angle, e.g., 45 degrees, so as to produce a crossing angle of 90 degrees. In certain embodiments, an intersection "point" may be scanned by a raster component 21 within a specific volume of a subject 22 in a set of x, y, and z planes in a predetermined pattern (see, e.g., FIG. 3A), so as to cause the crossed HEX-R beams 18a, 18b to describe a 3D image of one or more internal and/or external biochemical compositions of a subject 22, and their relative locations.

The two HEX-R beams 18a, 18b are not absorbed or retained within the subject 22. However, they do excite the atoms they pass through to yield secondary x-rays that describe the chemical constituents and their locations of the excited atoms. Collectively, the secondary x-rays (SX) are detected by detection equipment 24, while the beams 18a, 18b are absorbed at a dump 26. The detected SX yields an instantaneous and descriptive computer reconstructed 3DSX-Ray image (3DSXI) of the secondary x-rays emitted by the specified volume of the subject 22 under study. For example, the heart of the subject 22 may be scanned without scanning bones or lungs or other tissues proximate to the heart. The 3DSXI can be described in about a 20 nanosecond period. As such, the 3DSXI may be referred to as being produced nearly instantaneously.

Figure 3B:
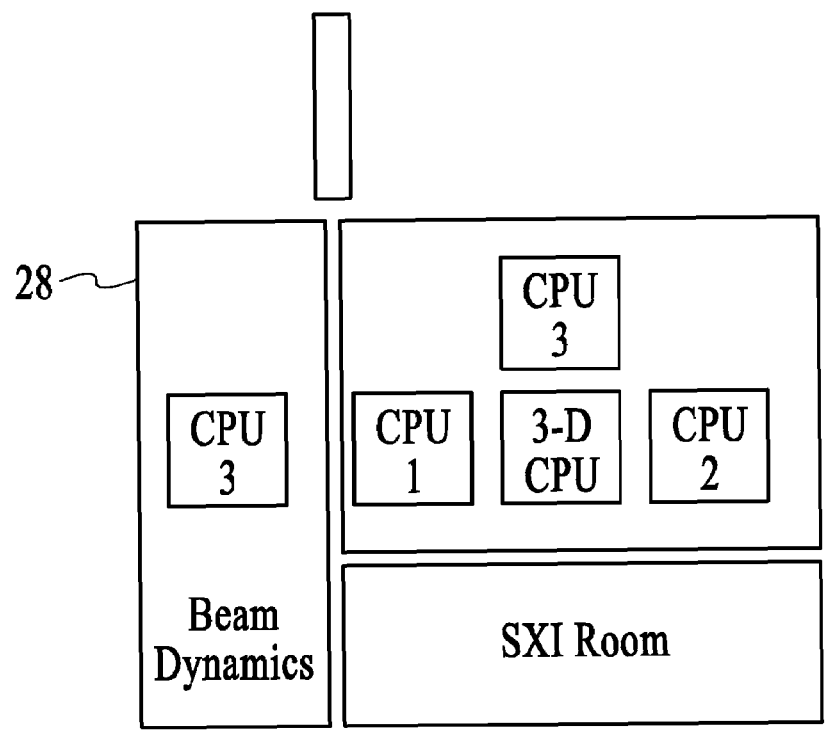
FIG. 3B illustrates a diagnostic network.

FIG. 3B illustrates a network of diagnostic equipment for obtaining a fluorescence image of a selected volume scanned with secondary x-rays. Computers CPU1, CPU2, CPU3 receive data from detectors oriented in three dimensions around a subject being scanned. The data is collected at 3-D CPU for generating a 3-D image of the volume with tissues having different properties showing different fluorescence characteristics being distinguished on a display. A beam dynamics component 28 monitors beam parameters for diagnoses of parameters of the scanning and/or fluorescence beams.

4D Secondary X-Ray Imaging (4DSXI)

By taking multiple 3DSXI's, e.g., of a pulsating heart of a subject 22, at successive, sub-incremental times, e.g., 0.1, 1, 10, 20, 50, 100, 200, 300, 400 or 500 milliseconds apart, or another selected duration or a second or more, the detected images yield a time related series of 3DSXI, hence a "4DSXI". For example, fifty thumbnail images may be generated at 20 millisecond intervals to achieve a series of images that show approximately a single beat of the heart, or a breath into the lungs, of the patient 22.

The 4D X-Ray System operates by sequentially tracking 3D X-Ray images at pre-determined intervals of time. Therefore, a 4D X-Ray of the heart would describe all of the internal physical actions such as blood flow rate, restrictions, and leakage if any, relative motion of valves, muscle contractions and expansions covering a single heartbeat. An advantageous 4D x-ray image of a beating heart would illustrate for a physician internal physical actions such as blood flow rate, restrictions, and leakage, if any, relative motion of valves, muscle contractions and expansions covering a dynamic heartbeat.

Advantages

Each time a bunch of electrons interacts with the standing wave, a cone or HEX-rays are generated. Thus, at very often and reliably predictable times, the HEX-rays are available for use as diagnostic physiological tools. This provides an ability to scan in raster fashion only a specified volume having discernible sub-tissue constituents. The scanning can occur many times in a short period of time to generate 3D and 4D images Secondary X-Ray Imaging (SXI) is a non-invasive method that can be used to image interior and/or exterior volumes of a subject. Hence, images may be acquired without surgically opening the subject or invading its surroundings.

The secondary x-ray images may be generated of interiors of small as well as large objects. The method is non-invasive, and so images can be taken without opening up the sample. This is an important consideration when dealing with living organisms (including human patients), and also with contraband searches and detection of forgeries or encoding of equity securities (such as stock certificates, bonds, Treasury bills, and currencies), or artwork, particle contamination of semiconductor substrates, and other objects that would be severely damaged by diagnostic invasion. An SXI image can reveal not only the interior structure, but also the material composition of an object. It can, therefore, answer questions such as: "what chemical elements are contained or encoded in sample under investigation, and where are they located?"

Secondary x-ray imaging (SXI) does not deposit residual radiation within the subject. It does not burn or destroy tissue, or create environments conducive to cancer. The beam of secondary x-rays passes through the subject, leaving behind useful component fluorescence signatures revealing interior structures of the subject, its chemical and bio-chemical compositions and details of where and how they are related.

The 3D X-Ray systems operate at the speed of light, at nano-second periods of time, and without the use of mechanical repositioning or restrictions on the subject. Whereas some imaging systems may utilize a 90-degree mechanical rotation of the subject or of the scanning equipment relative to the subject such as with MRI's and Cat Scans, the 3D x-ray system permits the subject and the bulky equipment to remain stationary during imaging.

Control of points of interaction is possible at all power levels via dynamic steering of the beam. Control over the output level of the interaction is also achieved by controlling spacings of intervals of high energy X-ray generation. Control of the standing wave can be such that interaction intervals may be set based on known intervals of cycles of electrons and the controlling of the standing wave via a shutter or beam steering optics. For example, interactions of the electrons with the standing wave may be permitted every cycle, or every two cycles or three cycles, etc. As illustrated at FIG. 1A, if two, or more, standing wave arrangements 6 and 6' are provided around the synchrotron ring, then multiple interactions per cycle are possible.

With magnetic steering, high energy x-ray beam splitting is achieve automatically at the plane of maximum high energy X-ray output, i.e., the ring-like halo where the HEX beam is split into two collimated beams.

X-ray images are achieved without the requirement that a patient ingest iodine or other heavy metals that can be themselves difficult for a patient to ultimately digest or excrete.

Ion implantation may also be implemented as a method of introducing medical drugs into the body without residual, unintended side effects. Such ion implants may have instantaneous, measurable, identifiable results.

The depth and extent of the focal point of the beams 18a, 18b is also controllable so that the spatial resolution of the image may be balanced against detectable signals levels.

ALTERNATIVE EMBODIMENT

Figure 2B:
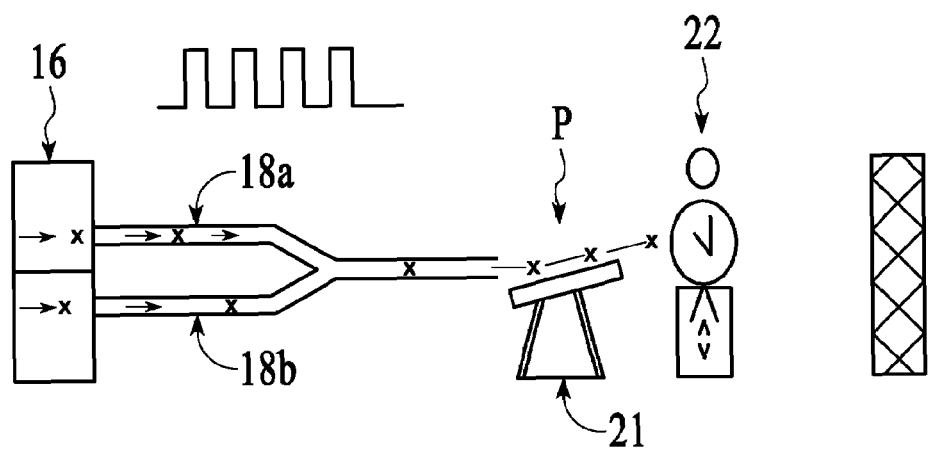
FIG. 2B is a side view of the magnetic steering section of FIG. 2A.

FIG. 5A is an overhead view which schematically illustrates a system for generating secondary x-rays in accordance with another embodiment. FIG. 5B is a side cross-section view of a particle beam-standing wave laser beam interaction portion of the system of FIG. 5A. High energy electron bunches 2 are generated in a synchrotron machine 4. Multiple standing wave laser beams 32 are present at the interaction point P. Multiple standing wave laser beams 32 may be used to extend the period of interactivity and/or to increase the overall power of the standing wave beams that are interacted with the electron bunches 2. The electron bunches 2 interact with each of the multiple standing wave laser beams 32 and generate cones of high energy x-rays. These are collected and collimated at 36. Multiple pairs of collimated rays are collected. For example, HEX's 38a and 38b are directed at a scan site 42, while HEX's 39a and 39b are directed at scan site 44 having similar component scanners and detectors as described above with reference to FIGS. 2A and 2B.

Figure 6:
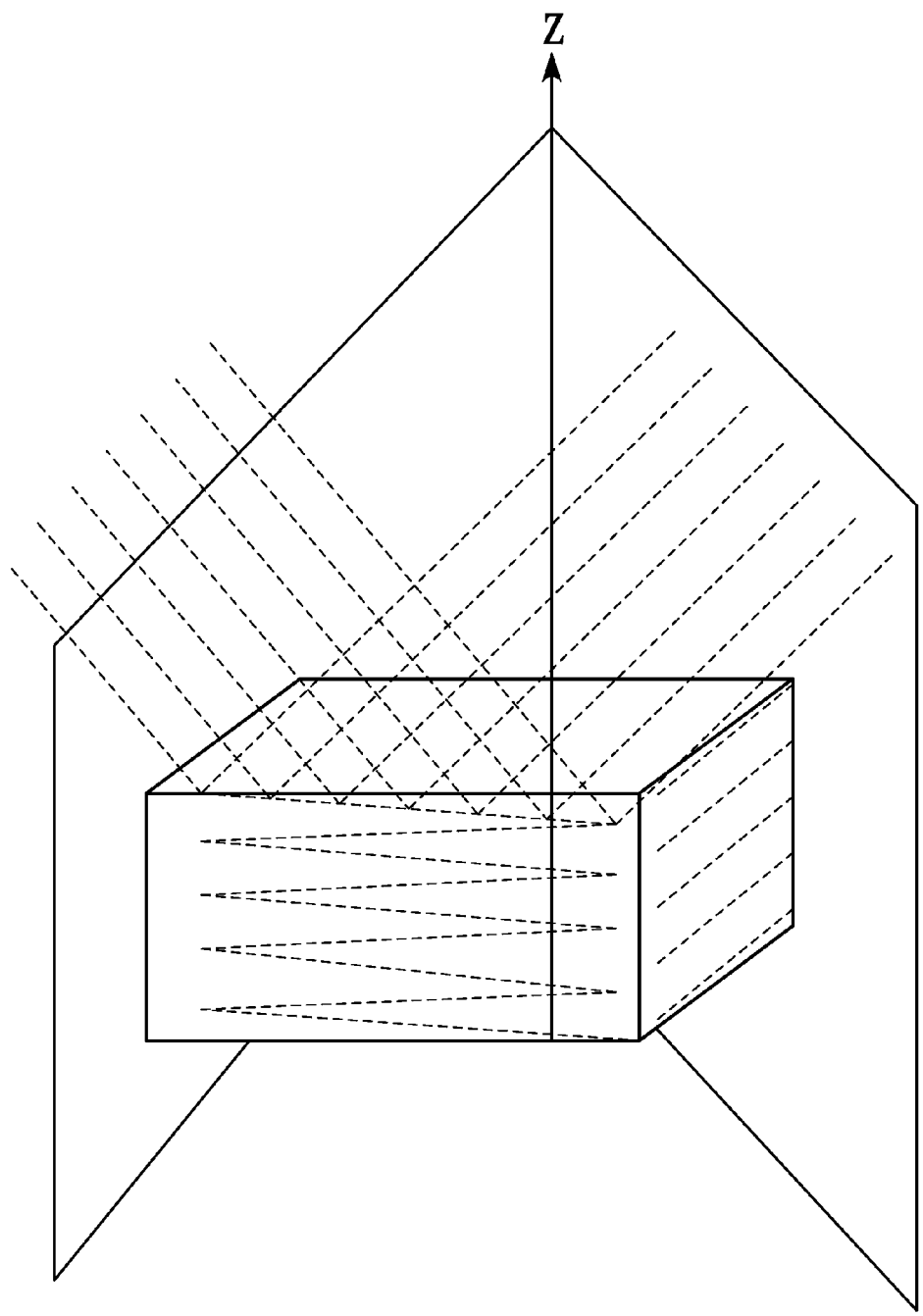
FIG. 6 illustrates scanning of a volume using two orthogonal scanning beams of high energy x-rays in accordance with an embodiment.

FIG. 6 illustrates scanning of a volume using two orthogonal scanning beams of high energy x-rays in accordance with an embodiment. Each of the beams 18a and 18b illustrated at FIGS. 2A and 2B impinges at a 45° angle, although these respectively angles may be varied. The volume is preferably vacuum enclosed, as is the rest of the beampath. Uniformity of intensity and direction of the two beams is thereby enhanced, such that the clarity and reliability of the 3-D chart prepared in accordance with the scanning will also be clear and reliable.

It is noted that the invention may be applied to scanning of human patients, animals or other living beings, food or other biological monitoring, nanotechnological diagnosis, security coatings, photolithography, ion-implantation and other practical uses wherein precise 3-D determinations of biochemical or material compositions of materials is desired.

That which is described as background, the invention summary, the abstract, the brief description of the drawings and the drawings, and all references cited or otherwise referred to above, are hereby incorporated by reference into the detailed description of the preferred embodiments as disclosing alternative embodiments.

While exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention, as set forth in the appended claims, and structural and functional equivalents thereof.

In addition, in methods that may be performed according to the claims below and/or preferred embodiments herein, the operations have been described in selected typographical sequences. However, the sequences have been selected and so ordered for typographical convenience and are not intended to imply any particular order for performing the operations, unless a particular ordering is expressly provided or understood by those skilled in the art as being necessary.

I claim:

1. A method of generating high energy x-rays, comprising:
   (a) generating a beam of electronic charges;
   (b) generating a standing wave laser beam;
   (c) colliding the beam of charges with the standing wave laser beam, including intersecting the standing wave laser beam and beam of charges to generate a burst cone of high energy x-rays;
   (d) detecting fluorescence spectra from interactions of the high energy x-rays with a patient's body to determine tissue properties;
   (e) generating a 3-D graphic which differentiates tissues having differing fluorescence characteristics; and
   (f) repeating the detecting to obtain temporal information (4-D).

2. A method of rendering a chart of a selected volume of a patient's body on a digital rendering device, display or printer, or combinations thereof, distinguishing fluorescence spectra from various points within the volume emitted as a result of interaction with high energy x-rays, the method comprising:
   (a) generating a beam of electronic charges;
   (b) generating a standing wave laser beam;
   (c) colliding the beam of charges with the standing wave laser beam, including intersecting the standing wave laser beam and beam of charges to generate a burst cone of high energy x-rays;
   (d) detecting fluorescence spectra resulting from interactions of the high energy x-rays with a patient's body which provide information regarding tissue properties;
   (e) generating 3-D graphic which differentiates tissues having differing fluorescence characteristics;
   rendering the 3-D graphic at a digital rendering device, display or printer, or combinations thereof; and
   (g) analyzing the fluorescence spectra to determine tissue properties.

3. The method of claim 2, further comprising repeating the detecting to obtain temporal information (4-D).

4. The method of claim 2, wherein said detecting is performed without rotating the patient relative to the propagation direction of the burst cones.

5. A system for generating high energy x-rays, comprising:
   an electron source for generating an electron beam; and
   a set of one or more lasers for generating a standing wave laser beam disposed in a path of the electron beam, wherein burst cones of secondary x-rays are generated from collisions between the electron beam and the standing wave laser beam;

a computer for analyzing fluorescence spectra from interactions of the high enemy x-rays with a patient's body to determine tissue properties; and computer readable programming code for generating a 3-D graphic formed from said interactions of the high energy x-rays with the patient's body.

6. The system of claim 5, wherein the electron source comprises a synchrotron radiation machine.

* * * * *